(12) United States Patent
Yodfat et al.

(10) Patent No.: US 9,597,451 B2
(45) Date of Patent: Mar. 21, 2017

(54) INSULIN DELIVERY SAFETY

(75) Inventors: Ofer Yodfat, Modi'in (IL); Gali Shapira, Haifa (IL); Iddo M. Gescheit, Tel-Aviv (IL)

(73) Assignee: Roche Diagnostic Operations, Inc., Indianapolis, IN (US)

( * ) Notice: Subject to any disclaimer, the term of this patent is extended or adjusted under 35 U.S.C. 154(b) by 1234 days.

(21) Appl. No.: 13/201,311

(22) PCT Filed: Feb. 11, 2010

(86) PCT No.: PCT/IL2010/000118
§ 371 (c)(1),
(2), (4) Date: Oct. 21, 2011

(87) PCT Pub. No.: WO2010/092572
PCT Pub. Date: Aug. 19, 2010

(65) Prior Publication Data
US 2012/0059352 A1 Mar. 8, 2012

Related U.S. Application Data
(60) Provisional application No. 61/152,514, filed on Feb. 13, 2009.

(51) Int. Cl.
*A61M 5/172* (2006.01)
*G06F 19/00* (2011.01)
*A61M 5/142* (2006.01)

(52) U.S. Cl.
CPC ........ *A61M 5/172* (2013.01); *A61M 5/14248* (2013.01); *G06F 19/3468* (2013.01);
(Continued)

(58) Field of Classification Search
CPC ......... A61M 2005/14208; A61M 2005/14268; A61M 5/14248; A61M 2209/01;
(Continued)

(56) References Cited

U.S. PATENT DOCUMENTS 6,936,029 B2  8/2005 Mann et al.
2002/0040208 A1* 4/2002 Flaherty ............ A61M 5/14248
604/288.01

(Continued)

FOREIGN PATENT DOCUMENTS

WO  WO 2009/125398  10/2009
WO  WO 2009/133558  11/2009

OTHER PUBLICATIONS

International Search Report and Written Opinion for PCT Application No. PCT/IL2010/000118.
(Continued)

*Primary Examiner* — Bhisma Mehta
*Assistant Examiner* — Larry R Wilson
(74) *Attorney, Agent, or Firm* — Dinsmore & Shohl LLP

(57) ABSTRACT

Embodiments of the present disclosure are directed to systems, devices/apparatuses and methods for assessing a residual insulin value for a user/patient. Such embodiments may be implemented by selecting a first value corresponding to a duration of insulin action; selecting a second value corresponding to a lock out time duration, selecting a first time period beginning at a time point T0 minus the first value and ending at the time point T0 minus the second value, selecting one or more boluses delivered during the first time period; for each of the one or more boluses selecting a corresponding residual insulin value estimated at the time point T0, computing the cumulative residual insulin value by summation of the corresponding residual insulin values.

20 Claims, 7 Drawing Sheets

(52) U.S. Cl.
CPC ........... *A61M 2005/14208* (2013.01); *A61M 2005/14268* (2013.01); *A61M 2005/14296* (2013.01); *A61M 2205/3523* (2013.01); *A61M 2205/502* (2013.01); *G06F 19/3437* (2013.01)

(58) Field of Classification Search
CPC ......... A61M 5/172; A61M 2005/14296; G06F 19/3437; G06F 19/3468
See application file for complete search history.

(56) References Cited

U.S. PATENT DOCUMENTS

| | | | |
|---|---|---|---|
| 2002/0169439 A1* | 11/2002 | Flaherty | A61M 5/14248 604/891.1 |
| 2003/0163088 A1 | 8/2003 | Blomquist | |
| 2007/0106218 A1 | 5/2007 | Yodfat et al. | |
| 2007/0191702 A1 | 8/2007 | Yodfat et al. | |
| 2008/0172031 A1* | 7/2008 | Blomquist | G06F 19/3468 604/500 |
| 2008/0214916 A1 | 9/2008 | Yodfat et al. | |
| 2008/0234663 A1 | 9/2008 | Yodfat et al. | |
| 2008/0319384 A1 | 12/2008 | Yodfat et al. | |
| 2010/0017141 A1* | 1/2010 | Campbell et al. | 702/19 |
| 2010/0256593 A1 | 10/2010 | Yodfat et al. | |

OTHER PUBLICATIONS

DCCT Trial, N. Engl J. Med 1993; 329: 977-986.
UKPDS Trial, Lancet 1998; 352: 837-853.
BMJ 1998; 317, (7160): 703-13.
EDIC Trial, N Engl J Med 2005; 353, (25): 2643-53.
Zisser, et al. Diabetes Technology and Therapeutics, 2008 10(6), p. 441-44.
Nucci et al., Computer Methods and Programs in Biomedics; 62 (2000), 249-257.

* cited by examiner

| Dose Given [IU] | Units left to work after: | | | | |
|---|---|---|---|---|---|
| | 1 Hr | 2 Hr | 3 Hr | 4 Hr | 5 Hr |
| 1 | 0.8 | 0.6 | 0.4 | 0.2 | 0 |
| 2 | 1.6 | 1.2 | 0.8 | 0.4 | 0 |
| 3 | 2.4 | 1.8 | 1.2 | 0.6 | 0 |
| 4 | 3.2 | 2.4 | 1.6 | 0.8 | 0 |
| 5 | 4.0 | 3.0 | 2.0 | 1.0 | 0 |
| 6 | 4.8 | 3.6 | 2.4 | 1.2 | 0 |
| 7 | 5.6 | 4.2 | 2.8 | 1.4 | 0 |
| 8 | 6.4 | 4.8 | 3.2 | 1.6 | 0 |
| 9 | 7.2 | 5.4 | 3.6 | 1.8 | 0 |
| 10 | 8.0 | 6.0 | 4.0 | 2.0 | 0 |

PRIOR ART
FIG. 1

INSULIN DELIVERY SAFETY

CROSS-REFERENCE TO RELATED APPLICATIONS

This application is a 35 U.S.C. §371 national stage entry of PCT/IL2010/000118, which has an international filing date of Feb. 11, 2010 and claims priority to provisional U.S. application Ser. No. 61/152,514, entitled "Increasing Safety of Insulin Delivery", filed on Feb. 13, 2009," the content of which are hereby incorporated by reference in their entireties.

FIELD

Embodiments of the subject disclosure are directed to methods, devices and systems for sustained infusion of fluids. Some embodiments are related generally to a portable insulin infusion apparatus and a method for bolus delivery based on the residual insulin computation/determination (each term being used interchangeably throughout the present disclosure).

BACKGROUND

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and secrete insulin according to the blood glucose levels, maintaining near constant glucose levels in the body.

Much of the burden of the disease to the user and to health care resources is due to the long-term tissue complications, which affect both the small blood vessels (microangiopathy, causing eye, kidney and nerve damage) and the large blood vessels (causing accelerated atherosclerosis, with increased rates of coronary heart disease, peripheral vascular disease and stroke). The Diabetes Control and Complications Trial (DCCT) demonstrated that development and progression of the chronic complications of diabetes are greatly related to the degree of altered glycemia as quantified by determinations of glycohemoglobin (HbA1c). [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53].Thus, maintaining normoglycemia by adequate insulin delivery can be of utmost importance.

Insulin infusion device can deliver rapid acting insulin (e.g. Lispro, Aspart, etc.) 24 hours a day through a cannula placed under the skin. Rapid acting insulin effect begins in about 10 minutes after administration, peaks at 1 to 1.5 hours after administration, and ends in about two to six hours after the administration. The duration of insulin action (DIA) is variable and thus this parameter can be set (programmed) in the pump by the user and/or caregiver.

A skin-securable insulin infusion device was disclosed in co-owned, U.S. patent application Ser. No. 11/397,115 (published as US2007/0106218) and International Patent Application No. PCT/IL06/001276 (published as WO2007/052277), and International Patent Application No. PCT/IL09/000388 (published as WO2009/125398) claiming priority to U.S. Provisional Patent Application No. 61/123,509, the disclosures of which are incorporated herein by reference in their entireties.

Insulin infusion device can be integrated with a continuous glucose monitor allowing open and closed loop systems (patient boluses at meals and automatic administration respectively). Such device integrating insulin delivery and glucose monitoring was disclosed in co-owned, U.S. patent application Ser. No. 11/706,606 (published as US2007/0191702) and International Patent Application No. PCT/IL07/000163 (published as WO2007/093981), co-owned, U.S. patent application Ser. No. 11/963,481 (published as US2008/0214916) and International Patent Application No. PCT/IL07/001579 (published as WO2008/078319), and co-owned International Patent Application No. PCT/IL08/001521 (published as the disclosures of which are incorporated herein by reference in their entireties.

One of the major advantages of insulin pumps is the convenience of insulin bolus administration at any desired time. However, the effect of boluses may overlap, hence the amount of active insulin that is still "working" in the body (hereinafter "residual insulin" or "RI") from previous boluses should be taken into account. Accumulation of insulin in the body, or "insulin stacking", may lead to life-threatening hypoglycemia. Prevention of hypoglycemia can be especially important (but not limited) at bedtime since users are typically unaware of nocturnal hypoglycemia.

A simple rule can be applied to calculate the RI. It is often stated that after bolus administration 20% of a dose is absorbed each hour, so that after 5 hours there is no active insulin remaining in the body. For example, FIG. 1 shows the insulin consumption according to the described rule (adapted from Using Insulin © 2003). Knowing the RI, can assist in providing the desired bolus dose. For example, if a 5 U bolus is planned 2 hours after a 6 U bolus [RI=6 U×0.2×2=3.6 U) the actual administered bolus should be only 1.4 U (5 U−3.6 U=1.4 U).

Most bolus recommendation tools, provided by different insulin pumps, can take the RI parameter into account. The recommended amount of insulin in the bolus to be delivered can be established, for example, by calculations, as described in U.S. Pat. Ser. No. 6,936,029 assigned to Medtronic MiniMed, or it can be selected by a method for selection of the desired bolus dose, as described in co-owned, International Application No. PCT/IL2008/000380 (published as WO2008/114254) and U.S. patent application Ser. No. 12/051,400 (published as 2008/0234663), the disclosures of which are incorporated herein by reference in their entireties. Some pumps (e.g., Deltec's, Insulet's) use linear plots to predict the residual insulin, while other pumps (e.g., Animas', MiniMed's) use curvilinear plots which better approximate the pharmacokinetics actions of insulin (Diabetes Technology and Therapeutics, 2008, 10(6), p. 441-44).

Most available bolus calculators take into account RI from boluses which have been administered during a time interval prior to a current bolus administration. Typically, this time interval does not exceed above the DIA, and the accumulated RI is subtracted from the current bolus dose to be delivered. Although insulin stacking can be prevented, this simple calculation of RI may lead to under-dosing if previous boluses administration times are very close to the current bolus administration time. For example, when a pump user eats a main course, he/she will first have to administer a bolus to balance the main course's carbohydrates. If the user further eats a desert 10 minutes after completing the main course, the pump and/or bolus calculator may indicate a high RI (resulted from the bolus administered prior to the main course to cover the main course) and may not require an additional bolus to cover the carbohydrates of the desert. Such indication can be misleading because the high RI may be sufficient to offset merely the main course but insufficient to offset the desert. The outcome of this miscalculation can lead to unbalanced offset of carbohydrates and subsequent hyperglycemia.

SUMMARY

Embodiments of the present disclosure are directed to systems, devices and methods for estimating residual insulin values. In some embodiments, such methods can be implemented according to one or more (and preferably all) of the following steps: selecting a first value corresponding to a duration of insulin action, selecting a second value corresponding to a lock out time duration, selecting a first time period beginning at a time point $T_0$ minus the first value and ending at the time point $T_0$ minus the second value, and selecting one or more boluses delivered during the first time period. The method may further include selecting a corresponding residual insulin value estimated at the time point $T_0$ for each of the one or more boluses, and computing the cumulative residual insulin value by summation of the corresponding residual insulin values.

In some embodiments, methods for estimating residual insulin values may include one or more (and preferably all) of the following steps (which may be in addition to the steps described above): selecting an estimated amount of carbohydrates consumed by a user, computing a first insulin bolus corresponding to the estimated amount of carbohydrates without considering a residual insulin parameter, and computing a second insulin bolus by subtracting the cumulative residual insulin from the first insulin bolus. Delivery of the second insulin bolus to a user can also be initiated. The user can also be provided with a recommendation message corresponding to the insulin bolus. In some embodiments, the duration of insulin action and the lock out time duration can be configured by a user. In some embodiments, the lock out time duration can be selected between one and sixty minutes.

Embodiments of the methods may include any of the features described above in relation to a system, as well as any one of the features set out in the present disclosure.

Some embodiments of the present disclosure may be implemented using a delivery device and/or system. For example, a delivery device may implement one and/or another of the disclosed methods and may include a delivery mechanism (e.g., a pump) and a tangible machine-readable storage medium: for example, a processor, and/or a memory (e.g., any memory: magnetic disc, optical disc, flash memory, and the like), including instructions for carrying out the one and/or another of the disclosed methods. These features may be enclosed within a housing, for example. The tangible machine-readable storage medium may be enclosed within a housing of a device adapted to communicate wirelessly with the delivery device (for example), and thus be part of a drug delivery system. The delivery device can comprise a disposable portion and a reusable portion, in which the disposable portion can include a reservoir.

Some embodiments include a portable therapeutic fluid delivery apparatus/device (each term used interchangeably throughout), which may also be part of a system. Such an apparatus may comprise a skin securable (e.g., adherable), portable therapeutic fluid delivery apparatus comprising pump, a reservoir, a processer and a memory. At least one of the memory and processer includes a plurality of computer instructions for carrying out operations on the processor for a method for computing a cumulative residual insulin value, according to any of the method embodiments disclosed in the present application. The method may also be performed on a processor of a second device (in addition to it being performed on the processor of the delivery apparatus, or in place thereof). In some embodiments, the apparatus/device or system may include a remote control and/or a sensor for monitoring body analytes (e.g., glucose, ketones).

Embodiments of the device, apparatus and system may include any of the features a switches/buttons located adjacent the GUI (for example). Other elements of the GUI may include:
  a second input element for selecting a bolus dose without considering RI values; and
  a third input element for selecting of at least one of: an amount of carbohydrates to be consumed by a user, a glycemic index (GI), a glycemic load (GL), type of insulin, and insulin absorption rate.

In such a GUI, the second output element may be used for visually presenting a first potion of the recommended bolus dose and a second portion of the recommended bolus dose. Moreover, the first input element may include scrolling functionality.

BRIEF DESCRIPTION OF THE DRAWINGS

FIG. 1 shows a table of residual insulin (RI) estimation 1-5 hours after bolus administration of 1-10 U of insulin Lispro;

DETAILED DESCRIPTION

Figure 2:
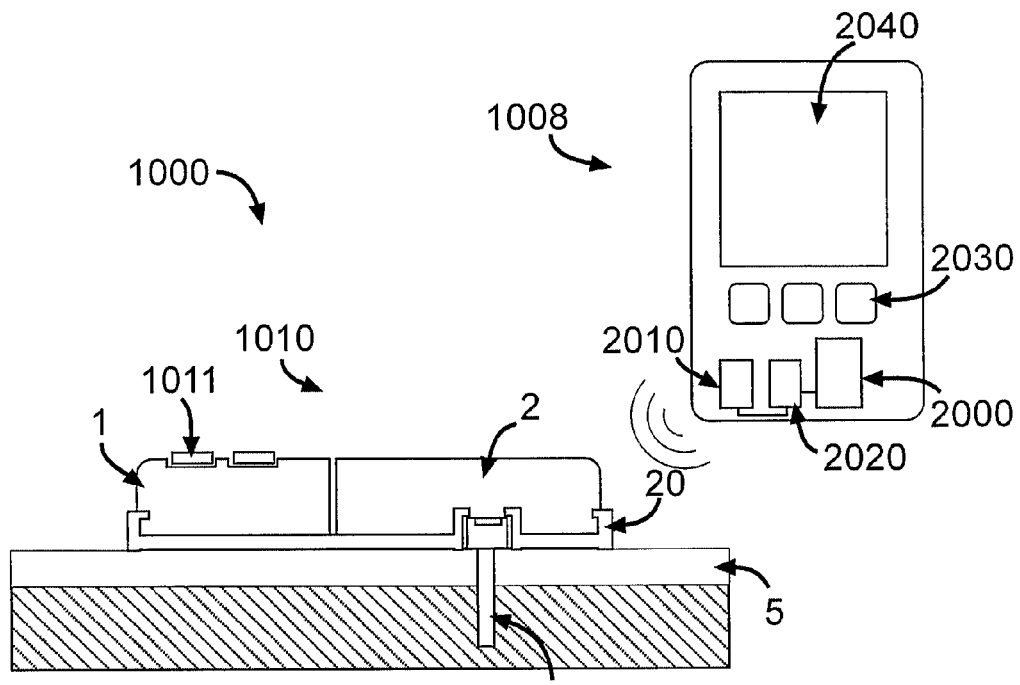
FIG. 2 illustrates an insulin infusion device for implementing a method for RI assessment according to some embodiments of the present disclosure.

Methods, systems and devices are provided herein for assessing a residual insulin (RI) value of a patient/user. Some embodiments can be implemented according to one or more (and preferably all) of the following steps: selecting a first value corresponding to a duration of insulin action, selecting a second value corresponding to a lock out time duration, selecting a first time period beginning at a time point $T_0$ minus the first value and ending at the time point $T_0$ minus the second value, selecting one or more boluses delivered during the first time period, for each of the one or more boluses—selecting a corresponding residual insulin value estimated at the time point $T_0$, and computing a cumulative residual insulin value by summation of the corresponding residual insulin values.

In some embodiments, a method for assessing the residual insulin value may be implemented via an infusion device comprises a dispensing patch unit (hereinafter the "patch"). In some embodiments, the patch can include two parts: a disposable part and a reusable part. In some embodiments, the infusion device can include a skin adherable cradle unit (hereinafter the "cradle"). In some embodiments, the infusion device can be part of an infusion system, which can further include a remote control unit (hereinafter the "RC"). The patch can be disconnected and reconnected from and to the cradle. A connecting lumen can provide fluid communication between the patch and a subcutaneously insertable cannula that can be rigidly connected to the cradle. Fluid delivery can be remotely controlled by the RC or by manual buttons/switches located on the patch.

Some embodiments provide a device (and corresponding system) that can deliver insulin into the body and can further monitor body (e.g. blood, interstitial fluid (ISF)) glucose levels. Some embodiments provide a method for RI assessment to prevent insulin under-dosing, hyperglycemia, and insulin stacking.

Some embodiments provide a device which is miniature, discreet, economical for users and highly cost effective. Such a device can implement a method for RI assessment to prevent insulin under-dosing, hyperglycemia, and insulin stacking (for example). For example, the device can contain a miniature skin securable (e.g., adherable to the skin) dispensing patch unit that can continuously dispense insulin and a method for RI assessment to prevent insulin under-dosing, hyperglycemia, and insulin stacking. The device can also comprise an insulin dispensing patch unit that can be remotely controlled and a method for RI assessment that can prevent insulin under-dosing, hyperglycemia, and insulin stacking. In some embodiments, the device can include a closed or semi-closed loop system that can sense and monitor glucose levels and dispense insulin according to the sensed glucose levels.

In some embodiments, the device can comprise a patch. For example, a patch can comprise a pumping mechanism (also referred-to as "pump", which may be any pump capable of conveying a liquid/fluid), reservoir and outlet port. The patch can be configured as a single part including a reservoir, one or more batteries, electronics (e.g., processor, memory, sensors), and a pump. The patch can also be configured as a two-part device, comprising a reusable part (hereinafter "RP") and a disposable part (hereinafter "DP").

For example, RP can comprise a motor, gear(s), electronics, and other relatively expensive components (e.g., an occlusion sensor). DP can comprise an outlet port, a reservoir, a slidable plunger (for example), a drive screw, and a nut. In some preferred embodiments the DP can contain at least one battery (e.g., Zinc air battery). In another embodiment, the reservoir can have a thin profile (e.g., oval, ellipse, four arches, etc.).

In some embodiments each one of the RP and DP can comprise a housing (shell, or pocket) and an insert (chassis) and upon RP-DP connection the housings and inserts can be coupled.

The device (or system) can also include a cradle. A cradle can be implemented as a flat sheet or otherwise structural member, with adhesive layer facing the skin provided with a passageway to a subcutaneously insertable cannula and snaps to secure the cannula and patch.

Some embodiments of the device (or system) described herein can also include a remote control unit ("RC"). The RC can be a handheld piece for programming fluid flows, controlling the patch, data acquisition, and providing indications (e.g., display, speaker, vibration mechanism). In some embodiments the RC can further comprise a wristwatch, cellular phone, PDA, smart-phone (e.g., iPhone), media player (e.g., iPod), and laptop (for example). The insulin infusion device can also be integrated with a continuous glucose monitor to allow open or closed loop systems.

In some embodiments, an assessed RI value can be used for bolus determination (or recommendations). For example, the RI can be calculated in accordance with boluses administered during a defined time period. In some implementations, the defined time period can last from the time of the current bolus administration minus the duration of insulin action "DIA" (e.g., 5 hours) until the time of the current bolus minus the lock-out time "LOT". In some embodiments, the LOT can be 15 minutes (for example). That is, the calculated RI can be derived from previous boluses given during the set DIA up to the lock-out time (e.g., from 5 hours before the current bolus until 15 minutes before the current bolus). The lock out time can prevent insulin under-dosing due to miscalculation of residual insulin which is supposedly remained from very recent administered boluses. Thus, for example, if an unplanned desert is eaten 10 minutes after the main course, the bolus delivered to cover the carbohydrates (or other consumables) of the main course will not be accounted for in the RI calculation.

According to some embodiments, during the defined time period between the DIA to the lock-out time (hereinafter "Effective Duration of Insulin Action" or "EDIA"), the RI can be calculated according to a linear plot, a curvilinear plot, or any other plot of insulin pharmacokinetics known in the art.

According to some embodiments, if a bolus is to be delivered, the RI can be subtracted from the bolus dose. In some embodiments, the method for assessing residual insulin values can be incorporated in the insulin infusion device.

FIG. 2 illustrates an exemplary insulin infusion system (1000), according to some embodiments, that can comprise a dispensing patch unit (1010), which can be adhered to the user's skin (5), and a remote control unit (1008), which can communicate with the dispensing patch unit (1010), allowing programming, user inputs and data acquisition. The remote control unit (1008) can be implemented as a dedicated remote control or in a cell phone, watch, Personal Data Assistant ("PDA"), laptop, iPod or any other device having wire or wireless communication capabilities such as RF, IR, magnetic, etc.

The patch unit (1010) can be attached to a cradle (20) that is a flat sheet or other structural member adhered to the user's skin (5) and can allow connection/disconnection of the patch unit (1010). During connection of the patch unit (1010) to the cradle (20), a connecting lumen can pierce a self sealed septum (e.g., rubber septum) in the cannula (6) providing fluid communication between the reservoir in the patch unit and subcutaneous tissue through the cannula (6).

In some embodiments, manual inputs can be carried out by one or more buttons/switches (1011) located on the dispensing patch unit (1010). The dispensing patch unit (1010) can be composed of two parts: a reusable part (1) and a disposable part (2) residing in one or two housings respectively.

According to some embodiments, the remote control unit (1008) can include an RI calculator (2000) for assessing the RI value, a processor (2010), a memory (2020), and a display/screen (2040). The display can communicate messages to the user, e.g., messages corresponding to bolus recommendation or RI values. Input means (2030) (e.g., buttons, switches, keys, keypad, icons, areas of a touch-sensitive screen, voice command, and the like) may also be provided. In some embodiments, communication with the user can be via a visual, audible or vibrational notification.

According to some embodiments, means (2000) for assessing the RI value (which may be a software application program run on a processor), and/or processor (2010), and/or memory (2020), and/or display (2040), and/or input means (2030) can be located in or on the dispensing patch unit (1010), particularly in the reusable part (1) of the dispensing patch unit (1010). According to some embodiments, the device/system (1000) can also comprise a blood glucose monitor and/or a continuous glucose monitor (CGM).

Figure 3:
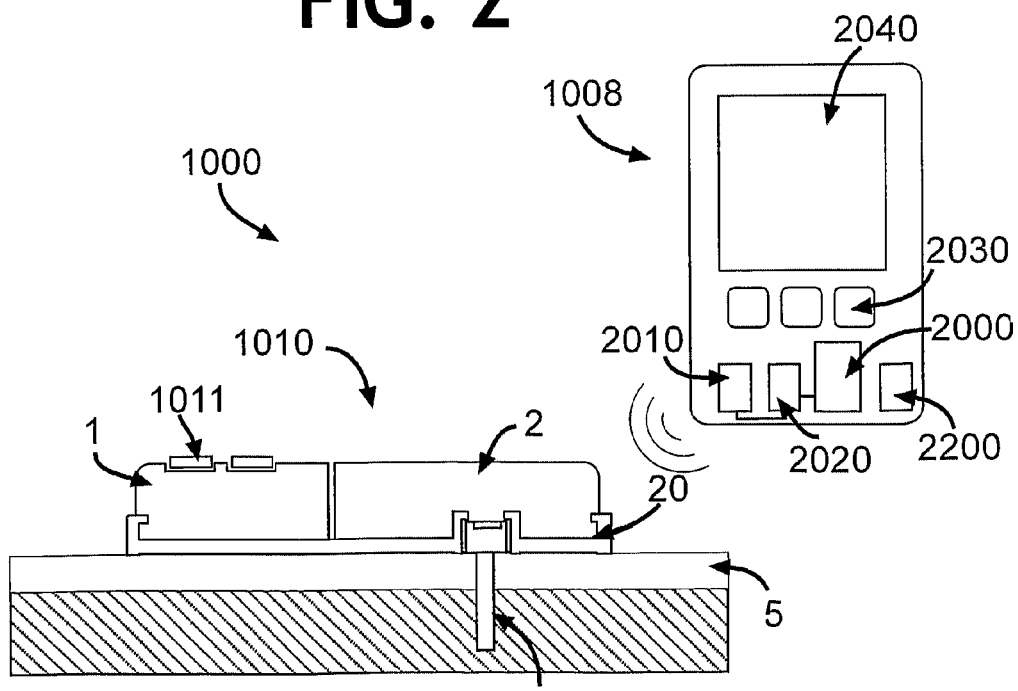
FIG. 3 illustrates an insulin infusion device configured to recommend a bolus dose in accordance with a method for RI assessment according to some embodiments of the present disclosure.

FIG. 3 illustrates one example of the insulin infusion device which includes a bolus recommendation device (2200) that provides a recommended bolus dose based on the RI value provided by the RI calculator (2000). The bolus recommendation device (2200) and RI calculator (2000) can be located in the remote control unit (1008).

According to some embodiments, the bolus recommendation device and/or the RI calculator can be located in the reusable part (1) of the dispensing patch unit (1010) or shared between the dispensing patch unit (1010) and the RC (1008).

Figure 4:
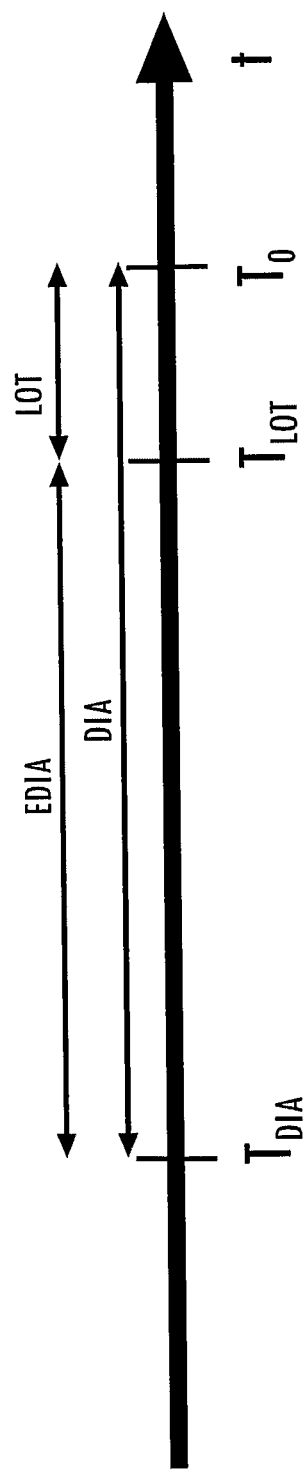
FIG. 4 is a time axis illustrating the EDIA.

In some embodiments, the assessed RI value can be used for bolus recommendations. For example, the RI can be calculated in accordance with boluses administered and or delivered during a defined time period. FIG. 4 shows a time axis (t) illustrating the EDIA (Effective Duration of Insulin Action). At the time of current bolus administration, $t=T_0$, the RI can be calculated. The boluses that account for the RI value can be those administered and/or delivered during the EDIA; the time period that falls between $T_{DIA}$ and $T_{LOT}$, i.e., EDIA=DIA−LOT. The time period between $T_{DIA}$ and $T_0$ is the duration of insulin action "DIA". The duration of insulin action is the period of time during which insulin dose is "active" in the body, i.e., offsets carbohydrates (for example) effect. In some embodiments, the DIA varies between 2 hrs and 8 hrs. The DIA may vary based on several factors, for example the type of insulin (e.g., Lispro, Aspart), physiological parameters of the user/patient (e.g., insulin absorption rate) and location (or site) of insulin administration. The time period that lasts between $T_{LOT}$ and $T_0$ is the lock-out time, or "LOT". The lock-out time period is the period of time prior to the current bolus administration and food intake (e.g., carbohydrates intake) during which the delivered insulin does not affect/offset the consumed carbohydrates. Typically, a delay may be present between administration of the bolus to the subcutaneous tissue and its effect in the blood tissue, e.g., due to insulin absorption kinetics. Various meal characteristics, such as the glycemic index (GI) of the meal and fat percentage of the meal, may also influence the period of time during which the insulin does not affect/offset the consumed carbohydrates. The absorption of carbohydrates of the ingested food can also lag behind the absorption of the insulin. Thus, the "free" insulin, or "residual" insulin may counteract/offset the carbohydrates that may not have been absorbed yet. In some embodiments, the LOT varies between 0 and 60 minutes. Thus, boluses administered during the LOT may not be taken into account in assessing the current RI value (but may be taken into account for future assessments). That is, the calculated RI can be derived from previous boluses given during the EDIA.

According to some embodiments, during the defined time period between the DIA to the lock-out time (hereinafter "Effective Duration of Insulin Action" or "EDIA"), the RI can be calculated according to a linear plot, a curvilinear plot, or any other plot of insulin pharmacokinetics known in the art.

In some embodiments, the DIA can be assessed by the user/caregiver based on the method and device described in co-owned, International Patent Application No. PCT/IL08/001444 (published as WO2009/060433), entitled "Assessing Residual Insulin Time", the disclosure of which is incorporated herein by reference in its entirety.

Figure 5A:
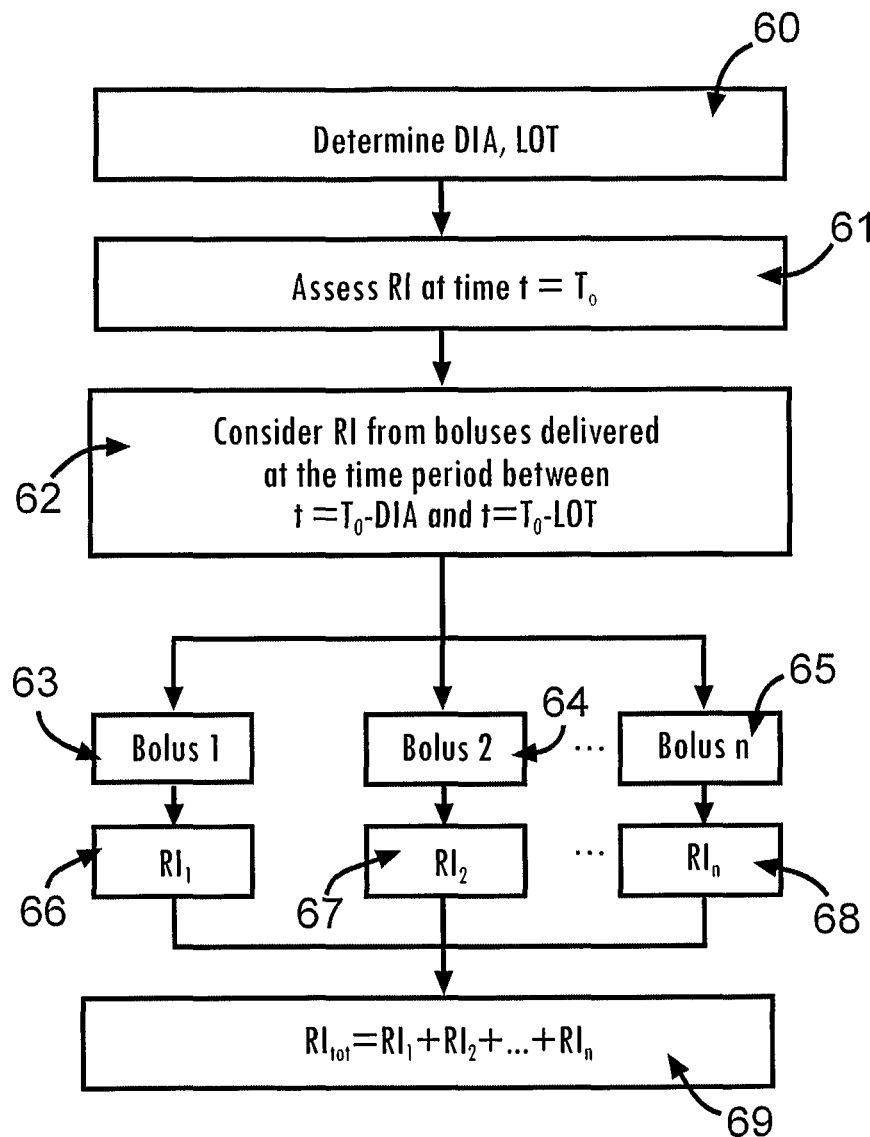
FIGS. 5a-b are block diagrams of an RI assessment method and a numerical example of the RI assessment method, respectively, according to some embodiments of the present disclosure.

FIG. 5a is a block diagram illustrating a method for assessing an RI value that can be implemented by the RI calculator according to some embodiments. At (60), the user/caregiver can set (or determine) at least one of the duration of insulin action (DIA), and the lock-out time period (LOT). The DIA can relate to the duration over which the insulin is being depreciated in the body. According to some embodiments, the user can set the DIA in the range of 2hr to 8hr with a 10-30 minutes step. According to some embodiments, a default DIA may be set (and stored in a memory), for example to 5 hrs. The LOT can relate to the most recent time period prior to the current RI assessment. Boluses that are being delivered during the LOT can be disregarded in the current RI value assessment (however data related to these boluses can be stored in a memory and retrieved in future occurrences). According to some embodiments, the user can set the LOT in the range of 0 to 60 minutes with a 1-30 minutes step. According to some embodiments, a default LOT may be set (and stored in a memory), for example to 10-60 minutes. Step (60) does not necessarily have to be performed in close proximity to the RI assessment. For example, DIA and LOT can be set once, and then being used every time that an RI is being assessed.

The RI value assessment can be initiated (61) at time $t=T_0$. At (62), the boluses delivered between time $T_{DIA}$ until time $T_{LOT}$ can be considered. In some embodiments, boluses delivered before $T_{DIA}$ and all boluses delivered after $T_{LOT}$, may not be considered for assessing the current RI value.

At (66)-(68), the RI can be calculated for boluses indexed as '1'-'n' (63)-(65), respectively ('n' representing an integer equal or higher than 1), wherein for boluses which were not administered/delivered during the EDIA, the corresponding RI would be zero. The RI can be calculated according to a linear plot, a curvilinear plot, or any other plot known in the art that reflects insulin pharmacokinetics. At (69), the separate RI values ($RI_1$, $RI_2$, . . . , $RI_n$) calculated in (66)-(68) can be summated to yield the final total RI value ($RI_{tot}$), also referred-to as "cumulative RI value".

The RI can be assessed based on at least one of a normal bolus (i.e., bolus delivered at the shortest time possible), long bolus (i.e., bolus delivered over an extended period of time), combination bolus (i.e., a combination of normal and long boluses), food bolus (i.e., a bolus that serves to cover a certain amount of carbohydrates in a meal), a correction bolus (i.e., a bolus that serves to bring the user from hyperglycemia back to target blood glucose levels), or a combination of any of the foregoing.

In some embodiments, a bolus may last longer than the DIA. In such a case, only the portion of the delivered bolus that falls within the EDIA will be considered in assessing the RI. For example, assessing an RI value at time 17:00 with a DIA of 3hrs, LOT of 10 minutes, and considering a long bolus which was administered at time 12:00 and lasts 3 hours. The portion of this long bolus taken into account when assessing the current RI would be based on the amount of insulin delivered between 14:00 and 15:00, for example. In other embodiments, the long bolus can be administered during the EDIA and last even after the current bolus administered at $T_0$. For example, assessing an RI value at time 17:00 with a DIA of 3 hrs, LOT of 10 minutes, and considering a long bolus which was administered at time 16:00 and lasts 3 hours. The portion of this long bolus taken into account when assessing the RI would be based on the amount of insulin delivered between 16:00 and 16:50. In such cases, wherein a portion of the bolus is considered, the remained bolus portion can be recorded in memory for future use, for example, to be considered in assessing the RI value for a subsequent bolus administration.

Figure 5B:
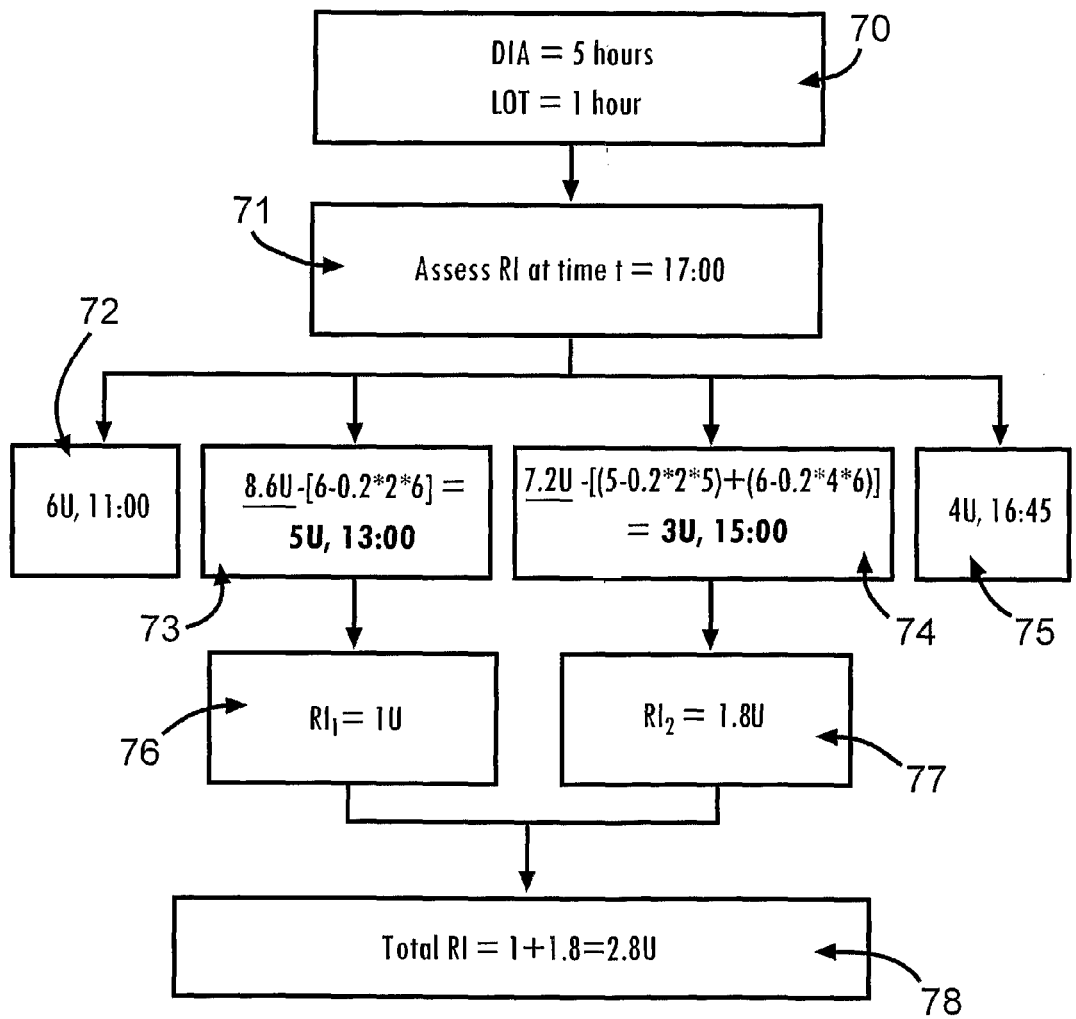

FIG. 5b illustrates a numerical example of the RI assessment method depicted in FIG. 5a. At (70) the user sets a DIA of 5 hours and a LOT of 1 hour. At (71) the RI is to be assessed at time 17:00. At (73) and (74) boluses delivered between 12:00 (17:00 minus DIA) and 16:00 (17:00 minus LOT) are depicted; a bolus of 5 U was delivered at time 13:00 (73) and a bolus of 3 U was delivered at time 15:00 (74). At (73) and (74), the underlined boluses (8.6 U and 7.2 U respectively) represent the boluses that would have been delivered had there been no RI. The computations/determinations in brackets ([6−0.2*2*6] and [(5−0.2*2*5)+(6−0.2*4*6)] respectively) represent the RI calculations performed according to a decaying linear curve in which 20% of the dose is consumed every hour (DIA of 5 hours), according to some embodiments.

At (76) and (77), the RI values of 1 U and 1.8 U may be calculated for the boluses at (73) and (74) respectively, according to a decaying linear curve in which 20% (i.e., 100/DIA) of the dose is consumed every hour (as depicted in FIG. 2). At (78), the total RI value, also referred-to as "cumulative RI value", is received by summation of the RI values calculated separately for each bolus, i.e., RI1 and RI2, calculated in (76) and (77), respectively. Boluses delivered before 13:00 (72) and after 16:00 (75) are not considered for the current RI value assessment (for example).

Figure 6A:
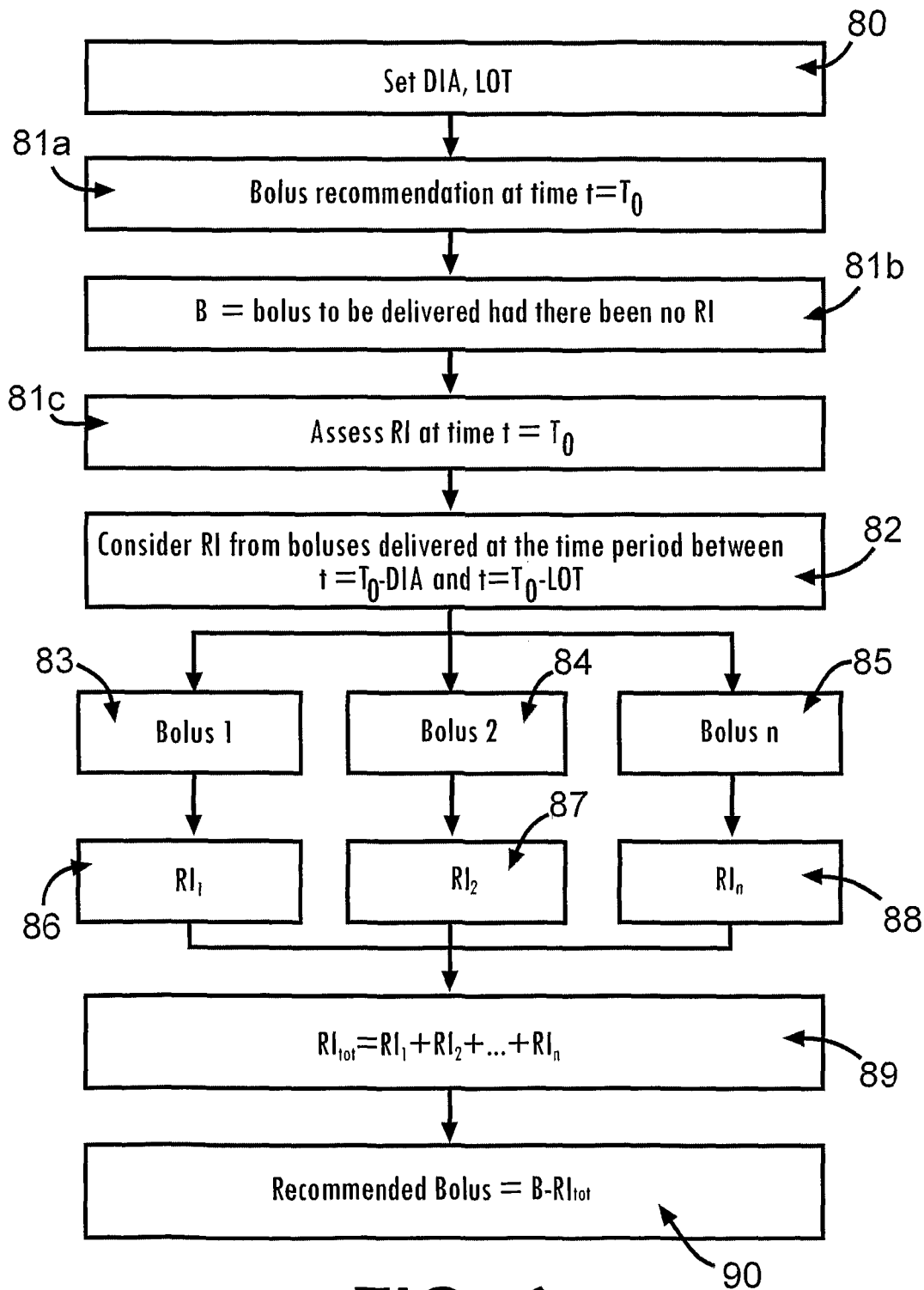
FIGS. 6a-b are block diagrams for bolus recommendation in accordance with an RI assessment method and a numerical example of bolus recommendation in accordance with an RI assessment method, respectively, according to some embodiments of the present disclosure.

FIG. 6a is a block diagram for bolus recommendation in accordance with the RI assessment method, according to some embodiments. For example, at (80), the user/caregiver sets the duration of insulin action (DIA), and the lock-out time (LOT) period. At (81a), a bolus calculation/recommendation is to be performed at time $t=T_0$. At (81b) a bolus (B) dose may be assessed, in some embodiments according to at least the user's current glucose level. The bolus (B) at this stage may be assessed without consideration of the RI value. The bolus can be directly estimated by the user or caregiver, calculated by a bolus calculator, or provided by a bolus recommendation tool such as the one described in co-owned, U.S. patent application Ser. No. 12/051,400 (published as US2008/0234663) and International Patent Application No. PCT/IL08/000380 (published as WO2008/114254), and International Patent Application No. PCT/IL09/000454 (published as WO2009/133558) claiming priority to U.S. Provisional Patent Application No. 61/048,856, the disclosures of which are incorporated herein by reference in their entireties. At (81c), an RI value assessment may be performed at time $t=T_0$. At (82), the boluses delivered between time $t=T_0-DIA=T_{DIA}$ until time $t=T_0-LOT=T_{LOT}$ may be considered. All boluses delivered before $T_{DIA}$ and after $T_{LOT}$ may not be considered for assessing the current RI value, i.e., their respective RI is set to zero for this assessment, but can be recorded in memory for calculation of future RI values (for example). At (86)-(88) the RI may then be calculated for boluses indexed as '1'-'n' (83)-(85), whereas 'n' represents an integer equal or higher than 1. At (89), the separate RI values are summated to yield the final total RI value ($RI_{tot}$), also referred-to as "cumulative RI value". At (90), the final bolus recommendation may be provided as the bolus (B) as provided at (81a) minus the total RI (i.e., $RI_{tot}$) as provided at (89). In some embodiments, the final bolus recommendation, as provided at (90), can be administered to a user, for example via a pump.

Figure 6B:
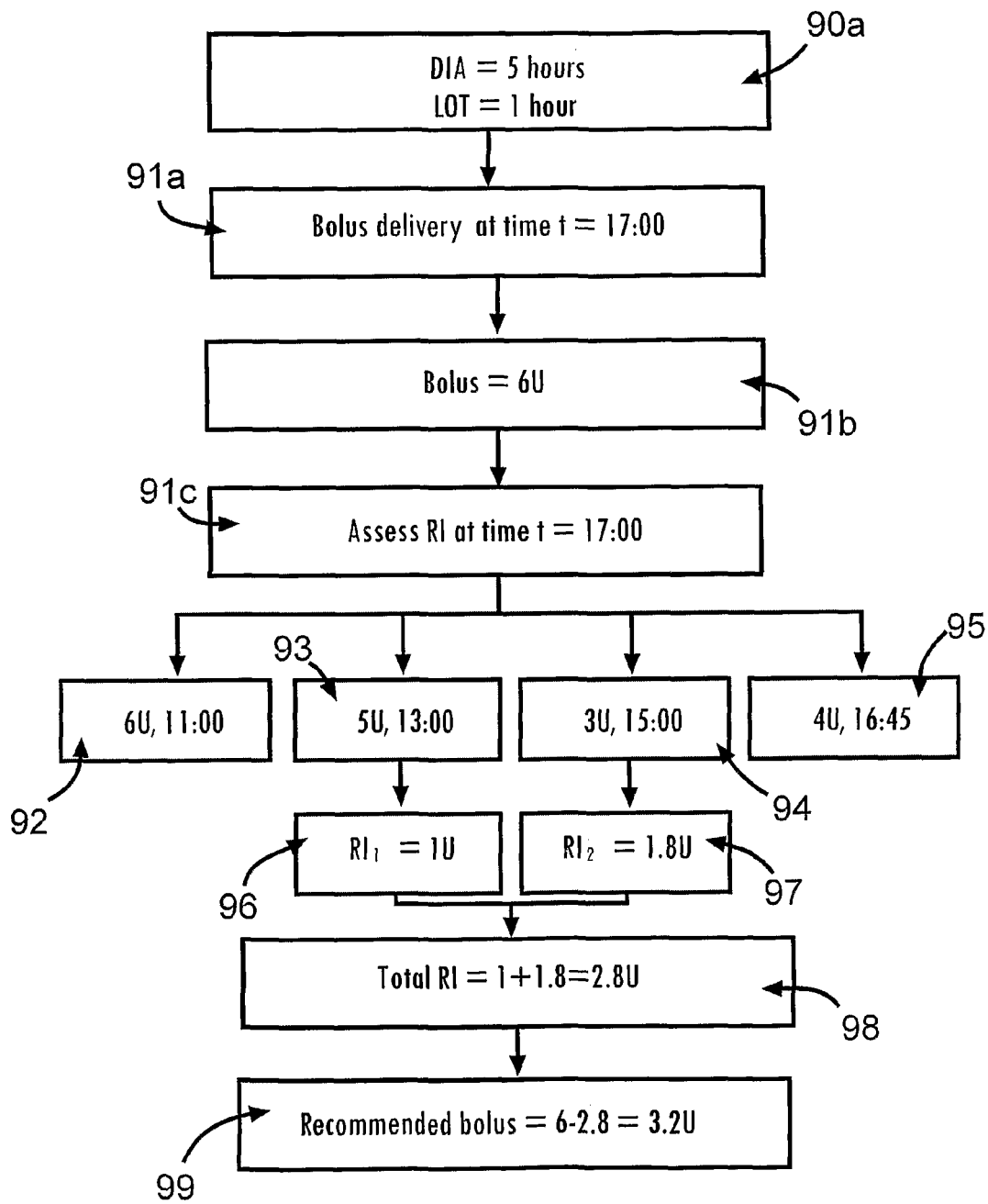

FIG. 6b shows a numerical example of bolus recommendation in accordance with the method depicted in FIG. 6a. At (90a) the user sets a DIA of 5 hours and a LOT of 1 hour. At (91a) a bolus is to be delivered at 17:00 to cover a planned meal. At (91c) the RI at the same time (designated as $T_0$) is to be assessed. At (91b) a bolus (B) dose of 6 U is determined (e.g., directly by the user, or by a bolus calculator). At (93) and (94) bolus doses (i.e., bolus doses after subtraction of RI) delivered between 12:00 (17:00 minus DIA) and 16:00 (17:00 minus LOT) are depicted; a bolus of 5 U was delivered at 13:00 (93) and a bolus of 3 U was delivered at 15:00 (94). At (96)-(97), corresponding RI values of 1 U and 1.8 U are calculated for the boluses at (93) and (94) respectively. The RI values can be calculated according to a decaying linear curve in which 20% (i.e., 100/DIA) of the dose is consumed every hour. At (98), the total RI value is received by summation of the RI values calculated separately for each bolus. Boluses delivered before 13:00 (92) and after 16:00 (95) are not considered for the current RI value assessment. At (99), a final bolus dose of 3.2 U is recommended based on the bolus (B=6 U) as provided at (91a) minus the total RI (2.8 U) as provided at (98). In some embodiments, the recommended bolus can be presented to a user via a screen (for example) and can be recorded in a memory. Then, the recommended bolus can be administered to a user, for example by using a pump.

In some embodiments, the LOT can relate to other parameters such as glycemic index (GI) or glycemic load (GL). A meal can correspond to a GI value which may be classified as ranges for example Low, Medium or High (e.g., GI value of yogurt, banana, and white bread respectively). The GI and LOT can obtain an inverse correlation, i.e., High GI (e.g., of white bread) may correlate with Low LOT (e.g., 10 minutes), and Low GI (e.g., of yogurt) may correlate with High LOT (e.g., 60 minutes). According to some embodiments, the GI values can be inputted by the user or retrieved from a memory or from a food database. The correlation can be based on a mathematical model or retrieved from a predetermined schedule which correlates GI values with LOT values.

In some embodiments, the LOT and/or RI values can be assessed based on a insulin pharmacokinetic model (e.g., model described by Trajanoski et al. (*Computer Methods and Programs in Biomedics;* 62 (2000), 249-257), herein incorporated by reference) which considers the insulin absorption in the subcutaneous tissue.

Various implementations of the subject matter described herein, such as the RI calculator and/or the bolus recommendation device, may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device, for example.

Such computer programs (also known as programs, software, software applications or code) include machine instructions for operation on a processor, and may be implemented in a high-level procedural and/or object-oriented programming language, and/or in assembly/machine language. As used herein, the term "machine-readable medium" or "tangible medium" refers to any computer program product, apparatus, system and/or device (e.g., magnetic discs, optical disks, memory, Programmable Logic Devices (PLDs), flash memory, and the like) used to provide machine instructions and/or data to a processor (e.g., a programmable processor), including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor and the like) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may also be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

Any and all references to publications or other documents, including but not limited to patents, patent applications, articles, webpages, books; etc presented and referenced in this specification are hereby incorporated by reference herein in their entireties. Although particular embodiments have been disclosed herein in detail, this has been done by way of example for purposes of illustration only, and is not intended to be limiting with respect to the scope of the appended claims, which follow.

It will thus be seen that many of the embodiments of the present disclosure attain objects made apparent from the preceding description. Since certain changes may be made without departing from the scope of the present disclosure, it is intended that all matter contained in the above description or shown in the accompanying drawings be interpreted as illustrative and not in a literal sense (and thus, not limiting). Practitioners of the art will realize that the method, device and system configurations depicted and described herein are examples of multiple possible system configurations that fall within the scope of the current disclosure.

While the disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the disclosure. All such modifications are intended to be within the scope of the claims appended hereto, as well as other claims which may be subsequently included in this or subsequent related filing. Other aspects, advantages, and modifications are also considered to be within the scope of the following claims.

What is claimed:

1. A method for delivering an adjusted insulin bolus into a body of a patient comprising:
    providing a remote control unit comprising a memory therein, the remote control unit communicative with a fluid dispensing unit comprising a reusable part and a disposable part, the disposable part containing a battery therein;
    selecting a first time corresponding to a duration of insulin action;
    selecting a second time corresponding to a lock out time duration;
    receiving input for a selection of a first time period beginning at a time point $T_0$ minus the first time and ending at the time point $T_0$ minus the second time;
    receiving input for a selection of one or more boluses delivered during the first time period;
    receiving input for a selection of a corresponding residual insulin value estimated at the time point $T_0$ for each of the one or more boluses;
    computing a cumulative residual insulin value based on the corresponding residual insulin values; and
    computing an adjusted insulin bolus based on the cumulative residual insulin value;
    wherein the residual insulin value estimated at the time point $T_0$ corresponds to a first portion of the one or more boluses, and the method further comprises recording, in the memory of the remote control unit, a second portion of the one or more boluses.

2. The method of claim 1, wherein selecting the first time comprises:
    receiving a first value corresponding to at least one of the first time and the duration of insulin action, and/or
    retrieving a first value corresponding to at least one of the first time and the duration of insulin action from the memory.

3. The method of claim 1, wherein selecting the second time comprises:
    receiving a second value corresponding to at least one of the second time and the lock out time duration, and/or
    retrieving a second value corresponding to at least one of the second time and the lock out time duration from the memory.

4. The method of claim 1, wherein selecting the first time period comprises receiving or computing the first time period at about the time point $T_0$.

5. The method of claim 1, further comprising receiving a request for dispensing an insulin bolus at about the time point $T_0$.

6. The method of claim 5, wherein the requested insulin bolus dose does not correspond to a residual insulin value.

7. The method of claim 1, wherein selecting the one or more boluses includes retrieving the one or more boluses from the memory.

8. The method of claim 1, wherein computing the cumulative residual insulin value includes summation of the corresponding residual insulin values.

9. The method of claim 6, wherein computing the adjusted insulin bolus further corresponds to the requested insulin bolus dose.

10. The method of claim 1, the fluid dispensing unit having one or more housings containing a pump and a reservoir, the pump being configured for dispensing the computed adjusted insulin bolus from the reservoir into a body of a user.

11. The method of claim 1, further comprising providing a processor, the processor having a bolus recommendation application operating thereon configured for computing the adjusted insulin bolus dose associated with the cumulative residual insulin value.

12. The method of claim 1, further comprising:
receiving an estimated amount of carbohydrates consumed or to be consumed by a user;
determining a first insulin bolus dose corresponding to the estimated amount of carbohydrates, without considering a residual insulin value, and
determining a second insulin bolus dose established by subtracting the cumulative residual insulin from the first insulin bolus.

13. The method of claim 1, wherein the lock out time duration corresponds to at least one of a glycemic index (GI), glycemic load (GL), type of insulin and insulin absorption rate.

14. The method of claim 1, wherein the duration of insulin action and/or the lock out time duration are configurable by a user.

15. The method of claim 1, wherein the lock out time duration is selected between about one and about sixty minutes.

16. The method of claim 1, further comprising delivering the adjusted insulin bolus into the body of the patient.

17. The method of claim 1, wherein the method further comprises notifying the patient that the adjusted insulin bolus is about to be delivered.

18. The method of claim 1, wherein at least one of the one or more boluses and the computed adjusted insulin bolus is selected from the group consisting of a normal bolus, long bolus, combination bolus, food bolus, a correction bolus and any combination thereof.

19. A system for determining and delivering an adjusted insulin bolus into a body of a patient comprising:
a remote control unit comprising a memory therein, the remote control unit communicative with a fluid dispensing unit comprising a reusable part and a disposable part, the disposable part containing a battery therein;
the fluid dispensing unit comprising one or more integrally connected housings containing a pump and a reservoir,
a processor, the processor having a bolus recommendation application operating thereon configured for carrying out the following steps:
receiving a first time corresponding to a duration of insulin action;
receiving a second time corresponding to a lock out time duration indicative of a period of time directly prior to an administration of the adjusted insulin bolus and within the duration of insulin action;
receiving a first time period beginning at a time point $T_0$ minus the first time and ending at the time point $T_0$ minus the second time, wherein the first time period corresponds to an effective duration of insulin action;
receiving a selection of a plurality of boluses delivered during the first time period;
receiving a selection of a corresponding residual insulin value estimated at the time point $T_0$ for each of the boluses;
computing a cumulative residual insulin value based on the corresponding residual insulin values; and
computing an adjusted insulin bolus based on the cumulative residual insulin value,
wherein the pump is configured for dispensing the computed adjusted insulin bolus from the reservoir into the body of the patient; and
wherein the residual insulin value estimated at the time point $T_0$ corresponds to a first portion of the plurality of boluses, and wherein the memory on the remote control unit is configured to store a second portion of one or more boluses.

20. The system of claim 19, wherein:
the effective duration of insulin action corresponding to the first time period is indicative of a defined time period between a start of the duration of insulin action and a start of the lock out time duration;
the first portion of the plurality of boluses is associated with the first time period comprising the effective duration of insulin action; and
the second portion of one or more boluses is associated with a second time period outside of the first time period.

* * * * *